| United States Patent [19] | [11] Patent Number: 5,051,132 |
| Yamasaki et al. | [45] Date of Patent: Sep. 24, 1991 |

[54] LYOPHILIZED PREPARATION OF 6-(3-DIMETHYLAMINOPROPIONYL)FORSKOLIN

[75] Inventors: Emiko Yamasaki, Kawaguchi; Taka'aki Ohkuma, Yono, both of Japan

[73] Assignee: Nippon Kayaku Kabushiki Kaisha, Tokyo, Japan

[21] Appl. No.: 530,355

[22] Filed: May 30, 1990

[30] Foreign Application Priority Data

Jun. 15, 1989 [JP] Japan ................................. 1-150595

[51] Int. Cl.$^5$ ...................... A01N 43/08; A61K 31/34
[52] U.S. Cl. ........................................ 127/30; 514/468
[58] Field of Search ........................... 514/468; 127/30

[56] References Cited

U.S. PATENT DOCUMENTS

| 2,149,304 | 3/1939 | Masucci et al. | 167/78 |
| 4,661,162 | 4/1987 | Kurihara et al. | 106/162 |
| 4,804,548 | 2/1989 | Sharma et al. | 426/453 |
| 4,936,074 | 6/1990 | Graham | 53/471 |
| 4,956,391 | 9/1990 | Sapse | 514/810 |

FOREIGN PATENT DOCUMENTS

| 0116713 | 8/1984 | European Pat. Off. . |
| 0191166 | 8/1986 | European Pat. Off. . |
| 0193132 | 9/1986 | European Pat. Off. . |
| 0222413 | 5/1987 | European Pat. Off. . |
| 1357731 | 6/1974 | United Kingdom . |

Primary Examiner—John F. Niebling
Assistant Examiner—P. L. Hailey
Attorney, Agent, or Firm—Henry C. Nields

[57] ABSTRACT

A lyophilized preparation comprising 6-(3-dimethylaminopropionyl)forskolin, a buffer agent having a pH value of about 3 to about 6 when dissolved, and, as an optional ingredient, a sugar. The lyophilized preparation is excellent in resolubility and stable in both pH and residual percentage.

9 Claims, No Drawings

LYOPHILIZED PREPARATION OF 6-(3-DIMETHYLAMINOPROPIONYL)FORSKOLIN

FIELD OF THE INVENTION

This invention relates to a lyophilized preparation of 6-(3-dimethylaminopropionyl)forskolin expected as a therapeutic agent for the cardiovascular diseases such as heart failure.

BACKGROUND OF THE INVENTION 6-(3-Dimethylaminopropionyl)forskolin has already been known as disclosed in EP 222,413-A and the like.

The present inventors attempted to make this compound into an injection. As a result, it was found that this compound is unstable in the state of aqueous solution and hence it must be made into a powdery preparation such as a lyophilized preparation, and that this compound has a fault that a lyophilized preparation prepared merely by dissolving this compound into water and lyophilizing it lowers its resolubility in the lapse of time during storage.

SUMMARY OF THE INVENTION

In view of the above, the present inventors have studied a formulation by which the resolubility can be improved. As a result, it has been found that a lyophilized preparation comprising 6-(3-dimethylaminopropionyl)forskolin and a buffer having a pH value of about 3 to about 6 when dissolved satisfies the above-mentioned object. Based on this finding, this invention has been accomplished.

DETAILED DESCRIPTION OF THE INVENTION 6-(3-Dimethylaminopropionyl)forskolin used in this invention is generally used in the form of hydrochloride. According to this invention, however, it can also be used in the form of a free compound or in the form of an inorganic or organic acid salt as desclosed in EP 222,413-A. Hereinafter, these 6-(3-dimethylaminopropionyl)forskolin and its salts are generically referred to as "6-(3-dimethylaminopropionyl)forskolin".

As the buffer having a pH value of about 3 to about 6 when dissolved used in this invention, non-volatile acids and/or salts thereof are preferable. Said acids and salts are not critical so far as said acid is liquid or solid at an ordinary temperature and said acid and/or salt thereof is therapeutically usable and physiologically acceptable and has a buffering action in the pH range of about 3 to about 6 where 6-(3-dimethylaminopropionyl)forskolin keeps stable and exhibits a good solubility. Specifically, there may be mentioned inorganic acids and/or their alkali metal salts and alkaline earth metal salts such as phosphoric acid and/or its sodium salts, potassium salts, magnesium salts and the like; oxycarboxylic acids having 6 carbon atoms such as citric acid, gluconic acid and the like; dicarboxylic acids having 4 carbon atoms such as succinic acid, tartaric acid, fumaric acid, maleic acid and the like; and/or their alkali metal salts and alkaline earth metal (e.g. magnesium) salts. Combined use of two or more members of these acids and/or salts thereof is also allowable. The amount of said acid and/or salt thereof to be added to the preparation varies depending on the buffering capacity of said acid and/or salt thereof. However, it is usually 0.1 to 5 parts by weight, preferably 0.1 to 4 parts by weight and more preferably 0.2 to 3 parts by weight, per one part by weight of 6-(3-dimethylaminopropionyl)forskolin. pH value of the composition of this invention is usually about 3 to about 6, preferably about 3.5 to about 5.5, and more preferably 3.5 to 5.0, as expressed in terms of pH value of re-dissolved solution, i.e. pH of a solution prepared by again dissolving a lyophilized product into water.

If desired, a sugar and the like may be additionally added to the preparation of this invention. Examples of said sugar include sugar alcohols such as xylitol, inositol, sorbitol, mannitol and the like; and sugars such as maltose, lactose, sucrose and the like. By combined use of these sugars, pH change before and after the lyophilization can be made small. Combined use of xylitol is particularly preferable because it improves the solubility at the time of re-dissolution and it nearly completely eliminates the pH change before and after lyophilization. Additionally speaking, xylitol and sorbitol have hardly been used hitherto as an excipient for lyophilization because their aqueous solutions have a low eutectic point. Accordingly, it is an entirely unexpected fact that a good lyophilized preparation can be obtained according to this invention.

These sugars are used in an amount of about 0 to 30 parts by weight, preferably 0.1 to 20 parts by weight and more preferably 0.2 to 15 parts by weight, per one part by weight of 6-(3-dimethylaminopropionyl)forskolin.

In the lyophilized preparation of this invention, proportions of ingredients are as follows: Proportion of 6-(3-dimethylaminopripionyl)forskolin is 20 to 80%, preferably 30 to 80% and more preferably 30 to 60%. Proportion of buffer agent is 5 to 50%, preferably 5 to 40% and more preferably 5 to 25%. Proportion of sugar is 0 to 75%, preferably 0 to 60% and more preferably 20 to 50%.

The lyophilized preparation of this invention can be prepared by, for example, lyophilizing a buffered solution having a pH value of about 3 to about 6 and containing 6-(3-dimethylaminopropionyl)forskolin and a non-volatile acid and/or its salt and, if desired, a sugar. More concretely speaking, a non-volatile acid and/or its salt as a buffer agent, 6-(3-dimethylaminopropionyl)forskolin and optionally a sugar are dissolved into water for injection and pH of the resulting solution is adjusted to about 3 to about 6, preferably about 3.5 to about 5.5 and more preferably about 3.5 to 5.0 with sodium hydroxide or the like. Temperature at the time of dissolution is not critical, but room temperature is enough for the purpose of this invention. When a salt of non-volatile acid is used, it can occur at some pH value that 6-(3-dimethylaminopropionyl)forskolin does not completely dissolve into water for injection. In such a case, it may be dissolved by lowering pH value to about 5.5 or below by the use of hydrochloric acid or the like or a nonvolatile acid similar to the above. As a preferable formulation of the aqueous solution, 5 to 50 mg/ml, preferably 10 to 40 mg/ml, of 6-(3-dimethylaminopropionyl)forskolin, 5 to 20 mg/ml of non-volatile acid and/or its salt and 0 to 100 mg/ml, preferably 5 to 80 mg/ml, of sugar such as xylitol can be referred to.

By freezing the aqueous solution obtained above at a temperature of $-35°$ C. to $-50°$ C. and subliming off the water under reduced pressure, the lyophilized preparation of this invention can be obtained.

The lyophilized preparation thus obtained is usually re-dissolved into water for injection or the like and put to use as a transfusion or an injection.

WORKING EXAMPLES

EXAMPLE 1

A composition was prepared by adding 6-(3-dimethylaminopropionyl)forskolin and phosphoric acid to a water for injection so that their concentrations became 20 mg/ml and 5 mg/ml, respectively, and making a solution by adjusting pH to about 4.0 with sodium hydroxide. The composition thus obtained was dispensed into vials at a rate of 1 ml/vial, and then it was lyophilized to obtain Product 1 of this invention.

EXAMPLE 2

A composition was prepared by adding 6-(3-dimethylaminopropionyl)forskolin, xylitol and phosphoric acid to a water for injection so that their concentrations became 20 mg/ml, 20 mg/ml and 10 mg/ml, respectively, and making a solution by adjusting pH to about 3.5 with sodium hydroxide. The composition thus obtained was dispensed into vials at a rate of 1 ml/vial and lyophilized to obtain Product 2 of this invention.

EXAMPLE 3

A composition was prepared by adding 6-(3-dimethylaminopropionyl)forskolin, xylitol and phosphoric acid to a water for injection so that their concentrations became 20 mg/ml, 20 mg/ml and 10 mg/ml, respectively, and making a solution by adjusting pH to about 4.5 with sodium hydroxide. The composition thus obtained was dispensed into vials at a rate of 1 ml/vial and lyophilized to obtain Product 3 of this invention.

EXAMPLE 4

A composition was prepared by adding 6-(3dimethylaminopropionyl)forskolin and citric acid to a water for injection so that their concentrations became 20 mg/ml and 10 mg/ml, respectively, and making a solution by adjusting pH to about 4.0 with sodium hydroxide. The composition thus obtained was dispensed into vials at a rate of 1 ml/vial and lyophilized to obtain Product 4 of this invention.

EXAMPLE 5

A composition was prepared by adding 6-(3-dimethylaminopropionyl)forskolin, xylitol and citric acid to a water for injection so that their concentrations became 20 mg/ml, 20 mg/ml and 10 mg/ml, respectively, and making a solution by adjusting pH to about 4.0 with sodium hydroxide. The composition thus obtained was dispensed into vials at a rate of 1 ml/vial and lyophilized to obtain Product 5 of this invention.

EXAMPLE 6

A composition was prepared by adding 6-(3-dimethylaminopropionyl)forskolin, mannitol and citric acid to a water for injection so that their concentrations became 20 mg/ml, 20 mg/ml and 10 mg/ml, respectively, and making a solution by adjusting pH to about 4 0 with sodium hydroxide. The composition thus obtained was dispensed into vials at a rate of 1 ml/vial and lyophilized to obtain Product 6 of this invention.

EXAMPLE 7

A composition was prepared by adding 6-(3-dimethylaminopropionyl)forskolin, maltose and citric acid to a water for injection so that their concentrations became 20 mg/ml, 20 mg/ml and 10 mg/ml, respectively, and making a solution by adjusting pH to about 4.0 with sodium hydroxide. The composition thus obtained was dispensed into vials at a rate of 1 ml/vial and lyophilized to obtain Product 7 of this invention.

EXAMPLE 8

A composition was prepared by adding 6-(3-dimethylaminopropionyl)forskolin, lactose and citric acid to a water for injection so that their concentrations became 20 mg/ml, 20 mg/ml and 10 mg/ml, respectively, and making a solution by adjusting pH to about 4.0 with sodium hydroxide. The composition thus obtained was dispensed into vials at a rate of 1 ml/vial and lyophilized to obtain Product 8 of this invention.

EXAMPLE 9

A composition was prepared by adding 6-(3-dimethylaminopropionyl)forskolin, xylitol, disodium hydrogen phosphate and phosphoric acid to a water for injection so that their concentrations became 20 mg/ml 20 mg/ml, 6 mg/ml and 5 mg/ml, respectively, and making a solution by adjusting pH to about 4.0 with sodium hydroxide. The composition thus obtained was dispensed into vials at a rate of 1 ml/vial and lyophilized to obtain Product 9 of this invention.

REFERENCE EXAMPLE 1

A composition was prepared by adding 6-(3-dimethylaminopropionyl)forskolin to a water for injection so that its concentration became 30 mg/ml and making a solution by adjusting pH to about 4.0 with hydrochloric acid. The composition thus obtained was dispensed into vials at a rate of 1 ml/vial and lyophilized to obtain Reference Product 1.

REFERENCE EXAMPLE 2

A composition was prepared by adding 6-(3-dimethylaminopropionyl)forskolin and xylitol to a water for injection so that their concentrations became 30 mg/ml and 30 mg/ml, respectively, and making a solution by adjusting pH to about 4.0 with hydrochloric acid. The composition thus obtained was dispensed into vials at a rate of 1 ml/vial and lyophilized to obtain Reference Product 2.

Next, the excellent storage stability and improved resolubility of the present lyophilized preparation of 6-(3-dimethylaminopropionyl)forskolin composition will be demonstrated by way of an experimental example.

EXPERIMENTAL EXAMPLE

Each of the products of this invention mentioned in Examples 1 to 8 and control samples of Reference Examples 1 to 2 obtained by adjusting pH with a volatile acid followed by lyophilizing was stored under a severe condition of 65° C. for one month, after which its appearance, resolubility, pH and residual percentage of 6-(3-dimethylaminopropionyl)forskolin were measured. The residual percentage was measured by liquid chromatography. Based on these results, the samples were compared one another in stability.

Resolubility was determined by adding 4 ml of a water for injection to sample and examining readiness of dissolution of sample.

The results are summarized in the following Table.

TABLE

| Sample | pH just after preparing sample solution | After storage at 65° C. for one month | | | |
|---|---|---|---|---|---|
| | | Appearance | Re-solubility[1] | pH | Residual percentage[2] |
| Example | | | | | |
| 1 | 3.9 | | | 5.3 | 96.1 |
| 2 | 3.7 | | ⊚ | 3.7 | 98.3 |
| 3 | 4.7 | | ⊚ | 4.6 | 102.2 |
| 4 | 3.9 | | | 4.3 | 96.0 |
| 5 | 3.9 | | ⊚ | 4.7 | 97.0 |
| 6 | 3.9 | | | 4.3 | 97.1 |
| 7 | 3.9 | | | 4.3 | 97.8 |
| 8 | 3.9 | | | 4.4 | 97.0 |
| Reference Example | | | | | |
| 1 | 4.1 | | x | 6.2 | 98.3 |
| 2 | 4.0 | | x | 5.8 | 94.3 |

Notes:
[1]: ⊚ Rapid dissolution (4 ml),
Dissolution (4 ml),
x No dissolution (4 ml).
[2]: Quantity at the initial is taken at 100%.

It is apparent from this Table that the preparations of this invention all exhibit a good resolubility, while both the control samples are not good in resolubility. Further, the preparations of this invention are all small in the pH change before and after storage. The products prepared by using xylitol (Examples 2, 3 and 5) are most excellent in resolubility. Although no great difference is not recognized between control samples and samples of this invention in the point of residual percentage of 6-(3-dimethylaminopropionyl)forskolin, the highest stability is observed on samples prepared according to this invention by using a sugar.

As has been mentioned above, a preparation of 6-(3-dimethylaminopropionyl)forskolin excellent in resolubility and stable in both pH and residual percentage can be obtained according to this invention.

We claim:

1. A lyophilized preparation consisting essentially of 6-(3-dimethylaminopropionyl)forskolin and a buffer agent having a pH value of about 3 to about 6 when dissolved.

2. A lyophilized preparation according to claim 1, wherein proportions of ingredients in the preparation are 20 to 80 w/w % of 6-(3-dimethylaminopropionyl)-forskolin, 5 to 50 w/w % of buffer agent and 0 to 75 w/w % of sugar.

3. A lyophilized preparation according to claim 2, wherein said buffer agent is selected from the group consisting of a non-volatile acid, a salt of said acid and mixtures of said non-volatile acid and salt.

4. A lyophilized preparation according to claim 3, wherein said non-volatile acid is selected from the group consisting of phosphoric acid, an oxycarboxylic acid having 6 carbon atoms and a dicarboxylic acid having 4 carbon atoms, and wherein the salt of said acid is selected from the group consisting of an alkali metal salt and an alkaline earth metal salt of the acid.

5. A lyophilized preparation according to claim 4, wherein said oxycarboxylic acid having 6 carbon atoms is selected from the group consisting of citric acid and gluconic acid, said dicarboxylic acid having 4 carbon atoms is selected from the group consisting of succinic acid, tartaric acid, fumaric acid and maleic acid, said alkali metal salt is selected from the group consisting of sodium salt and potassium salt, and said alkaline earth metal salt is magnesium salt.

6. A lyophilized preparation according to claim 2, wherein said sugar is selected from the group consisting of xylitol, inositol, sorbitol, mannitol, maltose, lactose and sucrose.

7. A lyophilized preparation according to claim 1, wherein said preparation comprises 30 to 60 w/w % of 6-(3-dimethylaminopropionyl)forskolin, 5 to 25 w/w % of phosphoric acid and its sodium salt and 20 to 50 w/w % of xylitol, and its re-dissolved solution has a pH value of 3.5 to 5.0.

8. A lyophilized preparation according to claim 1, further comprising sugar.

9. A lyophilized preparation according to claim 6 wherein said sugar is xylitol.

* * * * *